US00PP14169P39

(12) United States Plant Patent
Stöckmann

(10) Patent No.: US PP14,169 P3
(45) Date of Patent: Sep. 23, 2003

(54) PINE TREE NAMED 'BLUE ANGEL'

(75) Inventor: Ernst Adolf Stöckmann, Bad Zwischenahn (DE)

(73) Assignee: Jeddeloh Farms, Gresham, OR (US)

( * ) Notice: Subject to any disclaimer, the term of this patent is extended or adjusted under 35 U.S.C. 154(b) by 0 days.

(21) Appl. No.: 10/014,463

(22) Filed: Dec. 8, 2001

(65) Prior Publication Data

US 2003/0110544 P1 Jun. 12, 2003

(51) Int. Cl.[7] ..... A01H 7/00

(52) U.S. Cl. ..... Plt./213

(58) Field of Search ..... Plt./213

*Primary Examiner*—Bruce R. Campell
*Assistant Examiner*—June Hwu
(74) *Attorney, Agent, or Firm*—C. A. Whealy

(57) ABSTRACT

A distinct cultivar of Pine tree named 'Blue Angel', characterized by its uniform and upright plant habit; silvery blue green-colored leaves; and excellent garden performance.

1 Drawing Sheet

BOTANICAL CLASSIFICATION/CULTIVAR DESIGNATION

*Pinus parviflora* cultivar Blue Angel

BACKGROUND OF THE INVENTION

The present Invention relates to a new and distinct cultivar of Pine tree, botanically known as *Pinus parviflora,* and hereinafter referred to by the name 'Blue Angel'.

The new Pine tree is a naturally-occurring whole plant mutation of the *Pinus parviflora* cultivar Glauca, not patented. The Inventor discovered the new Pine tree as a single plant within a population of plants of the parent 'Glauca' in a controlled environment in Zwischenahn, Germany during the summer of 1964. The selection of this new Pine tree was based of its silvery blue green-colored leaves.

Asexual reproduction of the new Pine tree by scions grafted onto rootstocks of an unidentified selection of *Pinus strobus,* not patented, in a controlled environment in Zwischenahn, Germany, since 1970 has shown that the unique features of this new Pine tree are stable and reproduced true to type in successive generations.

SUMMARY OF THE INVENTION

Plants of the cultivar Blue Angel have not been observed under all possible environmental conditions. The phenotype may vary somewhat with variations in environment and culture such as temperature, light intensity, and daylength without, however, any variance in genotype.

The following traits have been repeatedly observed and are determined to be the unique characteristics of 'Blue Angel'. These characteristics in combination distinguish 'Blue Angel' as a new and distinct cultivar:

1. Upright and uniform plant habit.
2. Silvery blue-green-colored leaves.
3. Excellent garden performance.

Plants of the new Pine tree are most similar to plants of the parent, the cultivar Glauca. In side-by-side comparisons conducted in Zwischenahn, Germany, plants of the new Pine tree differed from plants of the cultivar Glauca, in the following characteristics:

1. Plants of the new Pine tree were more upright and not as broad as plants of the cultivar Glauca.
2. Plants of the new Pine tree were more freely branching and were denser and fuller than plants of the cultivar Glauca.
3. Plants of the new Pine tree grew more slowly than plants of the cultivar Glauca.
4. Leaves of plants of the new Pine tree were more silvery blue-green than leaves of plants of the cultivar Glauca.
5. Immature cones of the new Pine tree were purple in color whereas immature cones of the cultivar Glauca were green in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Pine tree.

The photograph at the top of the sheet comprises a side perspective view of a typical plant of 'Blue Angel' grown in the landscape.

The photograph at the bottom of the sheet comprises a close-up view of a typical branchlets and leaves of 'Blue Angel'. Plants in the photographs were about four to five years old.

DETAILED BOTANICAL DESCRIPTION

Plants used for the following observations and measurements were grown in Zwischenahn, Germany, in an outdoor nursery and under conditions which approximate commercial Pine tree production. Plants were grafted onto an unnamed selection of *Pinus strobus,* not patented, and were grown for about ten years.

In the following description, color references are made to The Royal Horticultural Society Colour Chart, 1966 Edition, except where general terms of ordinary dictionary significance are used.

Botanical classification: *Pinus parviflora* cultivar Blue Angel.

Parentage: Naturally-occurring whole plant mutation of the *Pinus parviflora* cultivar Glauca, not patented.

Propagation: By grafting scions onto rootstocks of an unidentified selection of *Pinus strobus,* not patented.

Plant description:

*Form.*—Upright and uniform perennial evergreen tree. Freely branching with lateral branches forming about every 5 to 10 cm. Each lateral branch with two to three branchlets. Moderately vigorous growth habit.

*Plant height.*—About 2.5 meters.

*Plant diameter.*—About 1 meter.

*Growth rate.*—Plants grow about 25 cm per year.

*Main trunk.*—Length: About 2.5 meters. Diameter, about 15 cm above the ground: About 9 cm. Strength: Strong. Texture: Woody, rough. Color: 195A.

*Primary lateral branches.*—Length: About 25 cm. Diameter: About 9 mm. Strength: Strong. Texture: Woody, rough. Color: 195A.

*Branchlets.*—Length: About 15 cm. Diameter: About 7 mm. Strength: Strong. Texture: Woody, rough. Color: 197A.

*Foliage description.*—Arrangement: In fascicles (clusters) of five. Length: About 8 cm. Width: About 1.5 mm. Shape: Acicular. Apex: Acute. Base: Sessile. Margin: Entire. Orientation: Lateral. Aspect: Twisting. Texture: Glabrous. Venation pattern: Linear. Fragrance: Slight; pine and honey-like. Color: Young foliage, upper and lower surfaces: 137A overlain with 122C. Fully expanded foliage, upper and lower surfaces: 137A overlain with 189A; overall tonality, close to 121C. Venation, upper and lower surfaces: Same as lamina.

Cone description:

*Natural flowering season.*—Typically late spring in Zwischenahn, Germany.

*Cones.*—Only female cones observed; roughly cylindrical covered with scales. Length: About 6.5 cm. Diameter: Before scales open: About 3.5 cm. With scales open: About 4.5 cm. Shape: Ovoid. Color: Immature: 185A. Mature: 177B.

*Seed.*—Quantity: Typically two seeds per scale. Length: About 1 cm. Diameter: About 5 mm. Shape: Ovoid. Color: 200D.

Disease/pest resistance: Plants of the new Pine tree have not been noted to be resistant to pathogens or pests common to Pine trees.

Weather tolerance: Plants of the new Pine tree have been observed to be tolerant to rain, wind and temperatures ranging from −22 to 40° C.

It is claimed:

1. A new and distinct cultivar of Pine tree named 'Blue Angel', as illustrated and described.

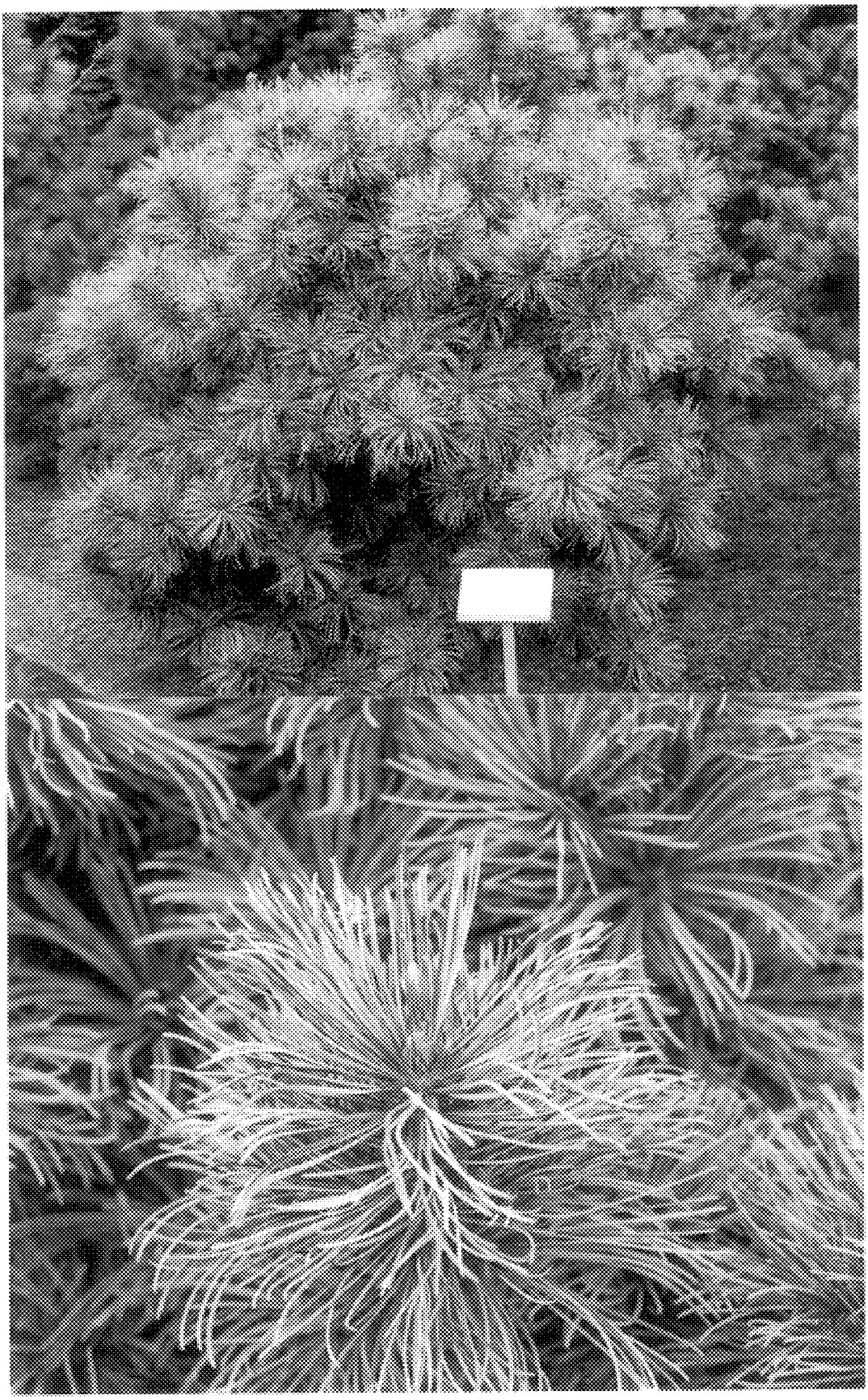

* * * * *